United States Patent [19]

Okusa et al.

[11] Patent Number: 4,952,520
[45] Date of Patent: Aug. 28, 1990

[54] IMMUNOASSAY MAKING USE OF LATEX AGGLUTINATION

[75] Inventors: Naoya Okusa; Taira Kanada, both of Tokyo, Japan

[73] Assignee: Daiichi Pure Chemicals Co., Ltd., Tokyo, Japan

[21] Appl. No.: 198,302

[22] Filed: May 25, 1988

[30] Foreign Application Priority Data

Jun. 5, 1987 [JP] Japan .................. 62-141236

[51] Int. Cl.⁵ .......................... G01N 33/546
[52] U.S. Cl. ................... 436/533; 436/523; 436/534; 436/805; 436/824
[58] Field of Search ............... 436/523, 533, 534, 805, 436/824

[56] References Cited

U.S. PATENT DOCUMENTS

| | | | |
|---|---|---|---|
| 4,184,849 | 1/1980 | Cambiaso | 436/523 |
| 4,353,984 | 10/1982 | Yamada et al. | 422/56 X |
| 4,419,453 | 12/1983 | Dorman | 436/533 X |
| 4,459,361 | 7/1984 | Gefter | 436/533 X |
| 4,639,419 | 1/1987 | Olson | 436/533 X |
| 4,745,075 | 5/1988 | Hadfield | 436/533 X |
| 4,828,980 | 5/1989 | Snyder et al. | 436/533 X |

FOREIGN PATENT DOCUMENTS

| | | |
|---|---|---|
| 0014965 | 9/1980 | European Pat. Off. . |
| 0217403 | 4/1987 | European Pat. Off. . |
| WO8404598 | 11/1984 | PCT Int'l Appl. . |

Primary Examiner—Robert J. Hill, Jr.
Attorney, Agent, or Firm—Oblon, Spivak, McClelland, Maier & Neustadt

[57] ABSTRACT

An immunoassay making use of latex agglutination is practiced by providing a colored latex as a latex, subjecting the colored latex to an immune reaction to form agglutinated particles of the colored latex, capturing the particles by means of a thin membrane with capillary-shaped pores formed therethrough, and then measuring the amount of the agglutinated particles thus captured.

2 Claims, 3 Drawing Sheets

IMMUNOASSAY MAKING USE OF LATEX AGGLUTINATION

BACKGROUND OF THE INVENTION (1) Field of the Invention

This invention relates to an improved immunoassay which makes use of latex agglutination.

(2) Description of the Related Art

Antigen-antibody reactions have been used widely for the diagnosis of diseases and the determination of infection.

However, antigen-antibody reactions themselves cannot be observed directly. A variety of attempts have hence been made with a view toward sensing such antigen-antibody reactions, resulting in the realization of agglutination reaction systems, agglutination inhibition reaction systems, methods making use of an enzyme or a radioactive substance, etc.

Of these, the agglutination reaction systems and agglutination inhibition reaction systems have merits such that they are extremely simple to practise, they do not require expensive instruments and they need shorter time for judgments. They are however accompanied by drawbacks such that difficulties are encountered in making a judgement as to the state of agglutination and they can hence be applied only to qualitative judgments. On the other hand, the methods making use of an enzyme or radioactive substance permit quantitative measurements and also feature high sensitivity. They however involve such drawbacks that their procedures are complex, they need reagents having poor stability and they require expensive instruments. Quantitative methods making use of latex agglutination have also found practical utility. One of the qualitative methods is to measure agglutination by a nephalometer, while the other is to measure the sizes of agglutinates by a particle-size-distribution measuring apparatus. Each of these methods however requires an expensive measuring apparatus and is hence not suitable for testing at work, emergency testing and testing at home.

Namely, among the conventional methods, the method relying upon visual observation is accompanied by drawbacks that (1) it is difficult to make a judgement and (2) it can only perform qualitative measurements. Although the methods making use of instruments can be employed for quantitative measurements, they are accompanied by drawbacks that (1) they need complex procedure and (2) the instruments are expensive and that they are hence not absolutely suitable for use at any places.

The present inventors had an expectation that a quantitative immunological assay would be feasible with ease and the above-described drawbacks could hence be solved provided that it would be able to collect only an agglutinated latex formed by an immunoassay making use of latex agglutination and then to measure its amount.

Incidentally, membrane filtration is a general method which has been known as a procedure for separating and capturing solute molecules of a relatively large particle size from smaller molecule solutes of about 0.05–2 $\mu$m. In general, the membrane has a network structure and its thickness ranges from 100 to 150 $\mu$m. When this membrane filtration was applied actually to agglutinated particles of a latex, the non-agglutinated latex which was supposed to pass through the membrane remained on the membrane because membrane pores were in the form of meshes and the membrane was thick. It was thus practically impossible to separate the non-agglutinated latex from the agglutinated latex. There was a further drawback that difficulties remain in directly measuring the amount of the thus-separated agglutinated particles of the latex.

SUMMARY OF THE INVENTION

Under the above-described circumstances, the present inventors have proceeded with a further investigation to solve the above drawbacks. As a result, it has been found that an agglutinated latex alone can be separated advantageously and its amount can be measured easily if colored latex particles are used as a latex and a thin membrane with capillary-shaped pores formed therethrough is employed as a membrane for membrane filtration, leading to the completion of this invention.

Namely, this invention provides an immunoassay making use of latex agglutination, which comprises providing a colored latex as a latex, subjecting the colored latex to an immune reaction to form agglutinated particles of the colored latex, capturing the particles by means of a thin membrane with capillary-shaped pores formed therethrough, and then measuring the amount of the agglutinated particles thus captured.

The immunoassay of this invention can be applied to both an antigen and an antibody as targets for measurement and in terms of the manner of a reaction, can be applied to both a competitive reaction (solid-phase method) and a non-competitive reaction (sandwich method).

Further, the present assay has inter alia the following merits.

(1) The color hue of colored latex agglutinates, whose color is to be measured, is vivid to the eye and is stable. (2) The procedure is easy for the separation of the agglutinated particle phase from the free particle phase and vice versa. In this case, no expensive measuring instruments are needed. The assay is feasible by means of a reflectometer under exposure to monochromatic light. (3) The time required for the assay is extremely short. (4) The measurement of trace levels is feasible by measuring reflectivities. (5) Compared to visual judgements, more objective judgements are feasible and the sensitivity becomes higher.

As has been described above, the immunoassay of this invention can solve or improve the drawbacks of the conventional immunoassays and its sensitivity is clearly higher than those of the conventional immunoassay. The immunoassay of this invention is therefore very useful as a testing method.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
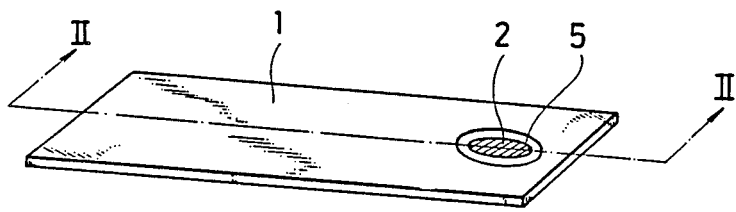
FIG. 1 is a perspective view showing one example of test pieces useful in the practice of the assay of this invention.
Figure 2:
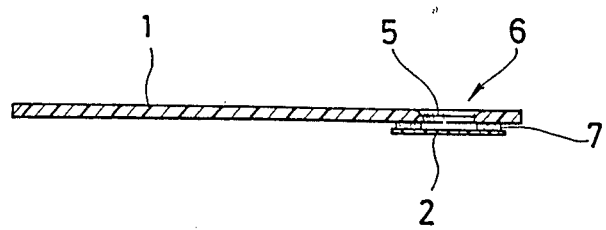
FIG. 2 is a longitudinal sectional view taken in the direction of arrows II—II of FIG. 1.

A commercial colored latex can be used as the colored latex to be used in the practice of the assay of this invention. It is possible to use, for example, "Estapole" (trade mark; product of Rhone-Poulenc, France) or the like. It is only necessary for such a colored latex to have a color hue such that the colored latex is clearly visible to the eye when captured on the membrane. The latex may preferably contain spherical particles which have a small particle size. As a specific particle size, about 0.1–1.0 $\mu$m is desirable in view of the sensitivity of immune reactions, agglutination due to an increased surface energy, etc.

Further, the thin membrane employed in this invention is far thinner than the conventional membranes and may preferably have a thickness of from 5 $\mu$m to 10 $\mu$m. As one example, may be mentioned a membrane marked in the trade mark of "Nuclepore Membrane" by Nuclepore Corporation, U.S.A. The suitable pore size of the membrane is determined by the particle sizes of latex particles and the sizes of agglutinated latex particles. Namely, each capillary-shaped pore is required to have a diameter such that latex particles are allowed to pass through the capillary-shaped pore but agglutinated latex particles are not allowed to pass therethrough. In general, the diameter may preferably range from 0.4 $\mu$m to 4.0 $\mu$m. As the material of the thin membrane, may be used, for example, plastics such as polycarbonate, ceramics, metal or the like. The filtration area of the thin membrane should be determined depending on the concentration of each sample to be tested. It is generally preferable to use a circular filtration area whose diameter ranges from 5 mm to 8 mm.

The latex agglutination in the assay of this invention is the same as conventional latex agglutination except for the use of a colored latex as a latex. The latex agglutination is carried out by using urine, serum, salivary or the like, which contains an antigen or antibody to be tested (tested substance), and a latex reagent containing an antibody or antigen for the tested substance. The membrane filtration of agglutinated latex particles, which have been formed by the latex agglutination, may be achieved by any known method, for example, by bringing the thin membrane with capillary-shaped pores into close contact with a perforated filter base or fiberglass filter paper having a large filtration flow rate so as to effect the filtration under a surface tension or by fixing the thin membrane on a filtration holder, connecting a syringe and a needle to the holder and effecting the filtration under a mechanical pressure.

Although the color hue of agglutinated colored latex particles which are captured on the thin membrane with capillary-shaped pores can be observed visually and qualitatively, their amount can also be determined by measuring the reflectivity under monochromatic light.

Having generally described the invention, a more complete understanding can be obtained by reference to certain specific examples, which are provided herein for purposes of illustration only and are not intended to be limiting unless otherwise specified.

EXAMPLES

Figure 3:
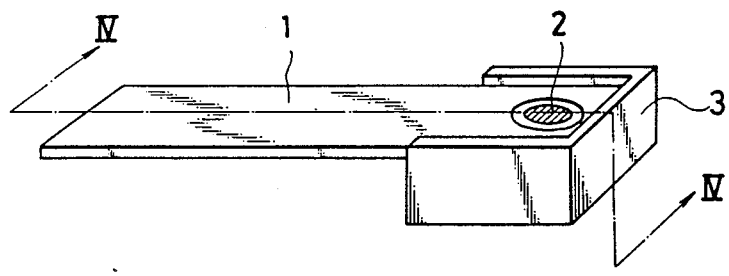
FIG. 3 is a perspective view illustrating the state of the exemplary test piece mounted on an adsorption bath.

This invention will next be described in further detail by the following Examples. Example 1:

(1) Instrumentation and test piece for membrane filtration:

A test piece shown in FIG. 1 was mounted for its application on an adsorption bath 3 as depicted in FIG. 3. The test piece was prepared by forming a hole 6, which was defined by a tapered peripheral edge portion 5 and had a diameter of about 6 mm, through one end portion of a carrier 1 and adhering and fixing a thin circular membrane 2 on one side of the carrier 1 at a location corresponding to the hole 6. The membrane 2 contains capillary-shaped pores, has a diameter of 13 mm, and is made of a polycarbonate (membrane with capillary-shaped pores having pore sizes not greater than 0.8 $\mu$m, thickness: 10 $\mu$m, porosity: $3 \times 10^7$ pores/cm$^2$; product of Nuclepore Corporation). The adhesion was effected using a double tack tape 7 ("TESA BAND", trade mark; product of Bayersdorf AG).

Figure 4:
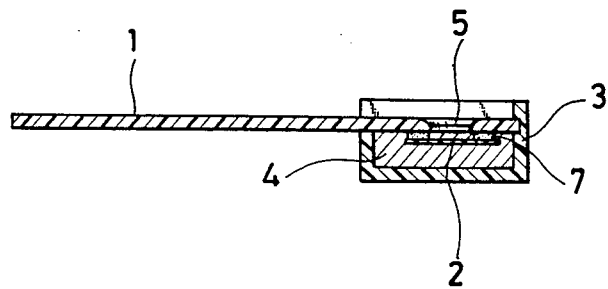
FIG. 4 is a longitudinal sectional view taken in the direction of arrows IV—IV of FIG. 3.

As indicated at FIG. 4, the adsorption bath 3 was filled with "Toyo Filter Paper No. 1034-3A" (trade name; which may alternatively be "Fiberglass Filter Paper GA-200" - trade name) as a filter base having a large filtration flow rate Membrane filtration was effected while maintaining the filter paper 4 in close contact with the thin membrane 2 through which the capillary-shaped pores are formed.

(2) Preparation of a red latex anti-hcG-$\alpha$-monoclonal antibody suspension (hcG-$\alpha$ detection reagent):

After quickly mixing 3.6 ml of 100 $\mu$g/ml anti-hcG-$\alpha$-monoclonal antibody with 1 ml of a 1% red latex (particle size: 0.23 $\mu$m) suspension which had been chilled to 4° C. in advance, the resultant mixture was left over at 4° C. for 2 hours. While stirring the liquid mixture, 4.6 ml of an albumin-containing tris buffer was added. After allowing the resultant mixture to stand at 4° C. for 2 hours, centrifugal washing was performed. The resultant product was added again with 4.6 ml of the albumin-containing tris buffer so as to suspend it again. Centrifugal washing was then effected. Thereafter, 4.6 ml of a tris buffer containing both sodium chloride and albumin was added to suspend the resultant product again. The suspension was left over at 37° C. for 2 hours. After washing it centrifugally, 6.3 ml of the tris buffer containing both sodium chloride and albumin was added to suspend the resultant product again, whereby a red latex anti-hcG-$\alpha$-monoclonal antibody suspension was prepared (3) Preparation of a red latex anti-hcG-$\beta$-monoclonal antibody suspension (hcG-$\beta$ detection reagent):

After quickly mixing 3.6 ml of 200 $\mu$g/ml anti-hcG-$\beta$-monoclonal antibody with 1 ml of a 1% red latex (particle size: 0.23 $\mu$m) suspension which had been chilled to 4° C .in advance, the resultant mixture was left over at 4° C. for 2 hours. The subsequent procedure was carried out in the same manner as in the preparation (2). Finally, 6.3 ml of the tris buffer containing both sodium chloride and albumin was added to suspend the resultant product again, whereby a red latex anti-hcG-$\beta$-monoclonal antibody suspension was prepared.

(3) Measurement:

The test piece described above under (1) was mounted on an adsorption bath filled with "Fiberglass Filter Paper GA-200" (trade name; product of Toyo Filter Paper Co., Ltd.) as a filter base.

Forty microliter portions of the hcG-α and hcG-β detection reagents obtained respectively in the above preparations (2) and (3) were measured and added to and mixed with 40 μl of a urine sample containing hcG antigen. After shaking the resultant mixture for 3 minutes, the thus-prepared liquid mixture was poured onto the thin membrane. Thereafter, 600 μl of an albumin-containing tris buffer was poured additionally. After the liquid passed through the thin membrane with capillary-shaped pores, the test piece was pulled out of the absorption bath and the thin membrane with capillary-shaped pores was exposed to monochromatic light of 540 nm to measure the reflectivity. The relationship between concentrations of hcG antigen and their corresponding reflectivities is shown in Table 1 and FIG. 5. Concentrations of hcG antigen were measured in the above manner.

Figure 5:
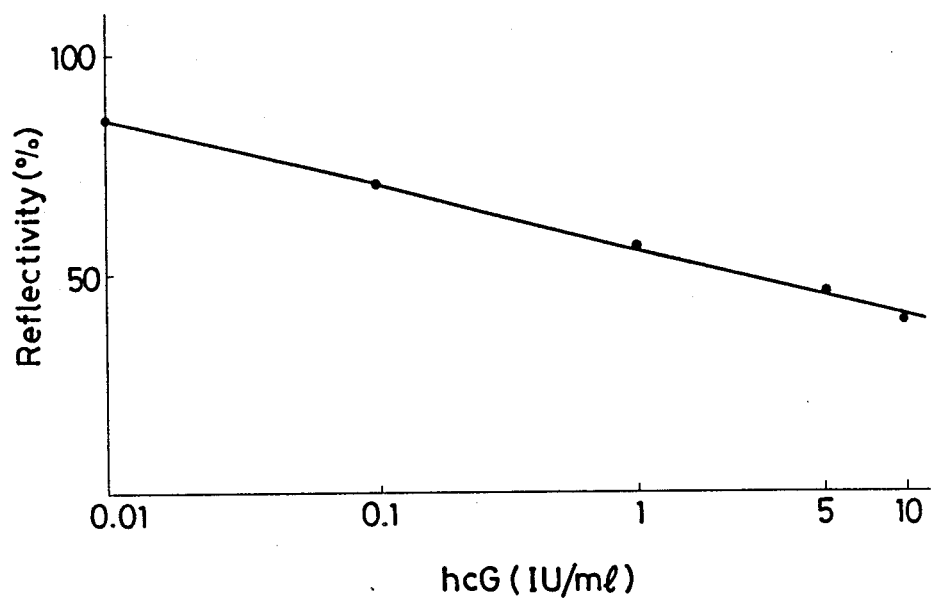
FIG. 5 is a diagrammatic representation shown the relationship between hcG concentrations and their corresponding reflectivities determined at 540 nm in accordance with the assay of the present invention.

(5) Results:

The relationship between the certain concentrations of hcG antigen and their corresponding reflectivities at 540 nm are shown in Table 1. A calibration curve drawn from these results is illustrated in FIG. 5, thereby making it clear that the assay of the present invention can be used as a quantitative assay.

TABLE 1

| hcG (IU/ml) | Reflectivity (%) upon exposure to light of 540 nm |
| --- | --- |
| 0.01 | 85.4 |
| 0.1 | 70.6 |
| 1.0 | 56.3 |
| 5.0 | 45.3 |
| 10.0 | 38.3 |
| 50.0 | 30.6 |
| 100.0 | 25.8 |

EXAMPLE 2

The reasonability of the filtration method making use of the thin membrane with capillary-shaped pores was investigated. The average particle size was measured by a particle-size measuring instrument both before and after the filtration, whereby the separation by the membrane with capillary-shaped pores was confirmed. As illustrated in Table 2, the particle size remained substantially the same both before and after the filtration in the case of the system free of hcG as an antigen, but a distinct difference was observed between the particle size before the filtration and that after the filtration in the case of the hcG-containing agglutination system, thereby confirming the capture of large particles on the membrane. In the present experiment, test pieces and hcG-α and hcG-β detection reagents were the same as those employed in Example 1. Those reagents were each added in an amount of 40 μl. Further, the membrane filtration was conducted under pressure by providing a syringe and a needle with a holder.

TABLE 2

| | Filtration | | |
| --- | --- | --- | --- |
| | Average particle size of agglutinated liquid before filtration | After filtration | |
| hcG (IU/ml) | | Color hue on membrane | Average particle size of filtrate |
| 0 | 228 nm | — | 222 nm |
| 10 | 649 | + | 247 |

EXAMPLE 3

The limit of detection of latex agglutination by the assay of this invention and that by slide agglutination* were compared visually. As the assay of this invention, agglutinated latex particles were prepared and collected by using the procedure and reagents (which were each used in an amount of 40 μl) described in Example 1. Results are summarized in Table 3.

* Slide agglutination: The state of agglutination is observed on a slide glass.

TABLE 3

| | Method | |
| --- | --- | --- |
| hcG concentration | Slide | Invention |
| 0.0 IU/ml | — | — |
| 0.01 | — | + |
| 0.1 | — | + |
| 1.0 | + | ++ |
| 5 0 | + | ++ |
| 10.0 | ++ | +++ |

As is apparent from the above results, the assay of the present invention has also higher sensitivity and excellent as a qualitative analysis compared with the conventional method.

We claim:

1. An immunoassay making use of latex agglutination, which comprises providing a colored latex as a latex, subjecting the colored latex to an immune reaction to form agglutinated particles of the colored latex, capturing the particles by membrane filtration while using a thin membrane with capillary-shaped pores formed therethrough, and then determining the amount of the agglutinated particles thus captured by measuring a reflectivity under exposure to monochromatic light.

2. The immunoassay as claimed in claim 1, wherein the capillary-shaped pores of the thin membrane have diameters in the range of 0.4 μm to 4.0 μm.

* * * * *